United States Patent
Blanke et al.

(10) Patent No.: US 6,198,009 B1
(45) Date of Patent: Mar. 6, 2001

(54) PERFLUOROPROPYLVINYLETHER PURIFICATION

(75) Inventors: John W. Blanke, Orange, TX (US); Julio A. Abusleme, Varese (IT)

(73) Assignee: Ausimont S.p.A., Milan (IT)

( * ) Notice: Subject to any disclaimer, the term of this patent is extended or adjusted under 35 U.S.C. 154(b) by 0 days.

(21) Appl. No.: 09/283,747

(22) Filed: Apr. 2, 1999

(30) Foreign Application Priority Data

Apr. 7, 1998 (IT) ............................................... MI98A0736

(51) Int. Cl.⁷ ..................................................... C07C 41/38
(52) U.S. Cl. ............................................. 568/682; 568/685
(58) Field of Search ..................................... 568/682, 685

(56) References Cited

U.S. PATENT DOCUMENTS

| 4,042,634 | | 8/1977 | Cope et al. | 210/616 |
| 5,239,055 | * | 8/1993 | Abe et al. | 528/493 |
| 5,352,785 | * | 10/1994 | Herzberg et al. | 544/178 |
| 5,618,894 | * | 4/1997 | DeSimone et al. | 526/89 |

FOREIGN PATENT DOCUMENTS 0 451 851 A1   10/1991   (EP) .

* cited by examiner

*Primary Examiner*—Rosalynd Keys
(74) *Attorney, Agent, or Firm*—Arent Fox Kintner Plotkin Kahn

(57) ABSTRACT

Perfluoropropylvinylether (FPVE) purification process with $C_1$–$C_{10}$ alcohols or mixtures thereof.

11 Claims, No Drawings

PERFLUOROPROPYLVINYLETHER PURIFICATION

The present invention relates to a perfluoropropylvinylether (FPVE) purification process. More particularly to a FPVE purification process of recovered FPVE from a fluoropolymer synthesis, which allows the reuse of FPVE in polymerization processes.

Fluoropolymer polymerization processes are known that use this monomer with the aim to improve the base characteristics of the polymer. For instance in tetrafluoroethylene (TFE), or ethylene/(E) TFE and/or CTFE (chlorotrifluoroethylene) polymers.

The FPVE reactivity is such that the amount of unreacted monomer after its use in a copolymerization process varies according to the polymer synthesis. Specifically its reactivity depends on the monomers involved, the pressure, the temperature, additives, solvents, chain transfer agents, etc., used in the synthesis The usual separation by distillation of unreacted monomers in polymerization does not always allow the recovery of the monomer free from residual substances used in the synthesis, for instance chain transfer agents, solvents or various additives, being this the case of FPVE. This situation becomes more critical when azeotropic compositions are formed between FPVE and undesired substances present in the polymerization process. For instance, in FPVE modified ECTFE copolymers where chloroform and/or methylcyclopentane and 1,1,2-trichloro-1,2,2-trifluoroethane (CFC-113) are present, distilled FPVE still contains solvent and chain transfer agents as impurities. Therefore the use of distilled FPVE limits the synthesis of materials containing very high molecular weight fractions. As known, this high molecular weight fraction imparts excellent mechanical properties at elevated temperatures as shown by high stress at break values which determine the thermal rating of the material. Consequently, the use of distilled FPVE for the synthesis of high performance ECTFE's is not possible.

More generally the presence of impurities in FPVE does not allow the monomer reuse in fluoropolymer synthesis. In this case its disposal is required leading to an unavoidable environmental impact. Besides, it is known in the art that the synthesis of FPVE is complex and therefore its efficient use is always recommended.

Therefore the need was felt to develop a purification process of FPVE to reduce the impurities such as solvents and chain transfer agents in order to allow the FPVE reuse in fluorinated polymers syntheses.

The Applicant has surprisingly and unexpectedly found a perfluoropropylvinylether (FPVE) purification process that consists in treating a FPVE phase containing contaminants with $C_1-C_{10}$ alcohols or mixtures thereof. $C_1-C_5$ alcohols or their mixtures are preferred. The more preferred are methanol and propanol.

The FPVE purification process according to the present invention is a treatment comprising one or more extractions or washings between liquid phases or liquid and gaseous phases.

When more extractions are carried out on the same FPVE solution to be treated, the subsequent extractions can be carried out with a fresh extracting phase or by recycling the extracting phase used in the first or previous treatments. More specifically the purification process is carried out by one or more extractions by using fresh alcohols or by recycling the alcohols already used in the previous extractions.

The ratio between the extracting phase and the FPVE phase to be purified varies according to the desired purity. Typically, when the starting contaminants amount is low the ratio between the extracting phase and the FPVE phase value is about 1:20 by weight, preferably 1:10 by weight. When the starting contaminants amount is at high levels the ratio between the extracting phase and the FPVE phase values is about 20:1 by weight, preferably 10:1 by weight.

The process of the invention is particularly suitable for the purification of unreacted FPVE, when its conversion in polymerization is lower than 80%. This is the case of the FPVE modified ECTFE polymerization.

As a matter of fact the FPVE modified ECTFE copolymers characterized by their high viscosity combined with excellent mechanical properties and processability, are synthesized by using practically no chain transfer agent at the beginning of the polymerization, but adding later to the reactor the chain transfer agent.

At the end of the polymerization there is a high amount of unreacted FPVE containing chain transfer agents. In order to recycle the FPVE it is necessary to clean it from the chain transfer agents. These chain transfer agents can be generally hydrogenated and/or halogenated compounds, e.g., methylcyclopentane, and chloroform which are substantially eliminated from the recovered FPVE using the purification process of the present invention.

The FPVE purification process of the invention can also be advantageously used when, as impurities, one or more polymerization solvents are present in general in an amount higher than 10% by weight in the recvovered FPVE. This leads to a change of the molar concentration ratios between the monomers in the reaction medium. The variations of molar ratio values between the monomers influence the monomer composition of the final product. An example of that is the purification of FPVE from CFC-113, solvent widely used in the fluoropolymer synthesis.

The purification process of the invention can be carried out by liquid-liquid or liquid-gas extraction either by a continuous process, or a semi-batch or a batch process. The liquid extracting phase is preferred.

The extracting agents used in the FPVE purification process of the invention are environmentally safe (low toxicity, easy disposal), non corrosive and they have a high extraction efficiency.

For extraction efficiency (or yield) of the alcohols it is meant the variation, normalized to hundred, of the percentage of the contaminants amount present in recovered FPVE that is to be purified, before and after the treatment:

initial wt % contaminants–final % wt % contaminants.100 initial wt % contaminants

The FPVE purification treatment can be also carried out with an extracting phase formed of a mixture of the above alcohols and $H_2O$. In this case a lowered extraction efficiency makes it necessary to conduct a greater number of washings relative to the use of pure alcohols.

It has been found by the Applicant that the FPVE purification process of the present invention can be applied for purifying a FPVE solution containing hydrogenated, halogenated and perhalogenated saturated or unsaturated residual substances.

The following examples are given to merely illustrate the invention but they are not limitative to the scope of the invention.

EXAMPLE 1

A solution-A containing 2% by weight of chloroform ($CHCl_3$) in perfluoropropylvinylether (FPVE) has been prepared by mixing 980 g of FPVE and 20 g of chloroform. In a separator funnel 30 g of methanol ($CH_3OH$) and 30 g of solution A have been introduced. After strong manual agitation for about 30 seconds and subsequent decantation to obtain two distinct clear phases; the heavier phase (FPVE phase) is separated and after sampling for chromatographic analysis it is collected in a suitable container. The methanol phase coming from previous extraction is used for further 8 times, following the above steps, every time using a fresh amount of solution A to be treated. In Table 1, the weight percentage compositions of chloroform solutions in FPVE after the treatment with the methanol extracting agent, are reported. In Table 2 the percentage extraction yield, that is the variation of the percentage by weight of[]chloroform extracted by methanol from the FPVE solution at every washing step, is reported.

The data reported in Table 1 show that the reuse of alcohol extracting solution coming from the previous extraction, even used many times, allows to reduce the chloroform amount in solution A.

The data of Table 2 show that the efficiency lowers when reusing the extracting solution used in the previous extractions.

EXAMPLE 2

Example 1 has been repeated by using n-propanol ($CH_3CH_2CH_2OH$) as extracting liquid. In Table 3, the weight percentage compositions of chloroform solutions in FPVE after the treatment with propanol are reported. In Table 4 the percentage extraction yield, that is the variation of the percentage by weight of chloroform extracted by propanol from the FPVE solution at every washing step, is reported.

EXAMPLE 3 (COMPARATIVE)

A solution A containing 2% by weight of chloroform ($CHCl_3$) in perfluoropropylvinylether (FPVE) has been prepared by mixing 980 g of FPVE and 20 g of chloroform. In a separator funnel 30 g of acetic acid ($CH_3COOH$) and 30 g of solution A have been introduced. After strong manual agitation for about 30 seconds and subsequent decantation till to obtain two distinct both clear phases, the lower phase (FPVE phase) is separated and after sampling for chromatographic analysis it is collected in a suitable container. The acetic acid phase coming from the previous extraction, is used for further 8 times, following the above steps, every time using a fresh solution A. In Table 5, the weight percentage compositions of chloroform solutions in FPVE after the treatment with the acetic acid extracting agent are reported. In Table 6 the percentage extraction yield, that is the variation of the percentage by weight of chloroform extracted by acetic acid from FPVE solution at every washing step, is reported.

For comparison, in Table 7, the compositions of the collected washed FPVE solutions of Examples 1, 2, and 3 are reported. As it is possible to note in the case of Example 3, both the extraction efficiency on chloroform and the final purity of FPVE phase are significantly low if compared with the results obtained with the alcohols of the present invention. Furthermore it is also possible to note that in this comparison Example the FPVE purity has not been improved, on the contrary it has decreased to 92% by weight (initial purity of 98%).

EXAMPLE 4

A solution B containing 5% by weight of chloroform ($CHCl_3$) and 11,1% by weight of methylcyclopentane (MCP) in perfluoropropylvinylether (FPVE) has been prepared. In a separator funnel 15 g of methanol ($CH_3OH$) and 30 g of solution B have been introduced. After strong manual agitation for about 30 seconds and subsequent decantation till to obtain two distinct clear phases, the heavier phase (FPVE phase) is separated and sampled for chromatographic analysis. The procedure just described is repeated, every time with a new amount of solution B, using different alcohols reported in Table 8. In the same Table, the weight percentage compositions of the FPVE solutions treated with the extracting agent are reported. In Table 9 the percentage extraction yields, that is the variation of the percentage by weight of chloroform and of methylcyclopentane extracted, by the alcohols from the FPVE solution, are reported.

EXAMPLE 5

A solution C containing 10% by weight of metylcyclpentane (MCP) in perfluoropropylvinylether (FPVE) has been prepared. In a separator funnel 30 g of ethanol ($CH_3CH_2OH$) and 30 g of solution C have been introduced. After strong manual agitation for about 30 seconds and subsequent decantation till to obtain two distinct clear phases, the heavier phase (FPVE phase) is separated and sampled for chromatographic analysis. The procedure just described is repeated for other three times with fresh ethanol on the same FPVE phase treated in the first extraction. In Table 10, the weight percentage compositions of the treated FPVE solutions are reported.

EXAMPLE 6

A solution A containing 2% by weight of chloroform in perfluoropropylvinylether (FPVE) has been prepared. In a separator funnel 30 g of ethanol ($CH_3CH_2OH$) and 30 g of solution A have been introduced. After strong manual agitation for about 30 seconds and subsequent decantation till to obtain two distinct clear phases, the heavier phase (FPVE phase) is separated and sampled for chromatographic analysis. The procedure just described is repeated for other three times with fresh ethanol on the same FPVE phase treated in the first extraction. In Table 11, the weight percentage compositions of the treated FPVE solutions are reported.

EXAMPLE 7

A solution D containing 10% by weight of methylcyclopentane (MCP) an 2% by weight of chloroform in perfluoropropylvinylether (FPVE) has been prepared. In a separator funnel 30 g of ethanol ($CH_3CH_2OH$) and 30 g of solution D have been introduced. After strong manual agitation for about 30 seconds and subsequent decantation till to obtain two distinct clear phases, the lower phase (FPVE phase) is separated and sampled for chromatographic analysis. The procedure just described is repeated for other three times with fresh ethanol on the same FPVE phase treated in the first extraction. In Table 12, the weight percentage compositions of the treated FPVE solutions are reported.

EXAMPLE 8

Two solutions have been prepared: the E solution being 33% by weight of 1,1,2-trichloro-1,2,2-trifluoroethane (CFC-113) in perfluoropropylvinylether (FPVE) and the other F solution being 170 by weight of CFC-113 in FPVE. In a separator funnel 30 g of methanol ($CH_3OH$) and 30 g of the E solution have been introduced. After strong manual agitation for about 30 seconds and subsequent decantation till to obtain two distinct clear phases, the heavier phase (FPVE phase) is separated and sampled for chromatographic analysis. The procedure just described is repeated with fresh methanol on the same FPVE phase treated in the first extraction. The same treatment is done with the solution F. In Table 13, the weight percentage compositions of the treated FPVE solutions are reported.

EXAMPLE 9

From the synthesis of FPVE modified ECTFE unreacted FPVE monomer is recovered and distilled. The distilled FPVE contains 0,9% by weight of $CHCl_3$.

A portion of this monomer is washed once with methanol using a 3:2 FPVE:methanol ratio. The treated FPVE contains 0,14% by weight of chloroform.

EXAMPLE 10

In an enameled autoclave equipped with baffles and stirrer working at 450 rpm, 4.3 l of demineralized water, 1.7 l (1.36 Kg) of methanol, 685 g of washed FPVE of Example 9 and 3 Kg of chlorotrifluoroethyhylene have been introduced. Autoclave has been heated to 5° C. and then ethylene was fed up to a pressure of 11.35 absolute bars. In the autoclave the radical initiator was then introduced, under the form of a solution, maintained at −17° C. of trichloroacethylperoxide (TCAP) in isooctane having a titre reported in Table 14, with a flow rate of 7.5 ml/hour up to an ethylene comsumption of 125 g. At this conversion 40 ml of chloroform have been introduced and subsequently the initiator flow rate was increased to 60 ml/hour.

The pressure was maintained constant during the polymerization by continuously feeding the ethylene up to a consumption of 250 g. Other reaction parameters, the Melt Flow Index (MFI) according to ASTM 3275-89 and the second melting temperature (Tm (II)) determined by differential scanning calorimetry (DSC) of the obtained polymer are reported in Table 14.

Mechanical properties at 175° C., reported in Table 14, have been obtained according to ASTM D1708, using compression molded plaques.

The shear viscosity (η) vs shear rate curve of the polymer has been determined at 275° C. according to ASTM D3835 in the range 1–1000 $s^{-1}$ from which the slope determined in the range 1–10 $sec^{-1}$ of shear rate has been deduced.

EXAMPLE 11 (COMPARATIVE)

Example 10 has been repeated in the same conditions but by using the distilled FPVE of Example 9. Reaction parameters, product characteristics and mechanical properties of polymer are reported in Table 14.

The use of a FPVE monomer practically free from chloroform (<0.2% by weight) in the polymer synthesis is absolutely necessary according to the results shown in Table 14. These considerations come from the fact that the stress at break at high temperature is significantly lower for the polymer obtained using the distilled FPVE of Example 9. The stress at break determines the thermal rating in use of the material; a decrease of the stress at break involves a lowering of the thermal rating of the material and therefore of its performance.

TABLE 1

Solution A composition ($CHCl_3$/FPVE) treated with $CH_3OH$

| Washing with $CH_3OH$ in 1:1 ratio by wt. with solution A | FPVE phase components | | |
|---|---|---|---|
| | $CHCl_3$ % w/w | $CH_3OH$ % w/w | FPVE % w/w |
| Initial | 2 | — | 98 |
| after I washing | 0.07 | 0.03 | 99.9 |
| after II washing | 0.14 | 0.16 | 99.7 |
| after III washing | 0.20 | 0.20 | 99.6 |
| after IV washing | 0.27 | 0.13 | 99.6 |
| after V washing | 0.37 | 0.13 | 99.5 |
| after VI washing | 0.40 | 0.10 | 99.5 |
| after VII washing | 0.47 | 0.13 | 99.4 |
| after VIII washing | 0.53 | 0.17 | 99.3 |
| after IX washing | 0.57 | 0.13 | 99.3 |

TABLE 2

| Washing with $CH_3OH$ in 1:1 ratio by wt with solution A | % weight variation of $CHCl_3$ (%) in FPVE phase |
|---|---|
| I washing | 96.5 |
| II washing | 93.0 |
| III washing | 90.0 |
| IV washing | 86.5 |
| V washing | 81.5 |
| VI washing | 80.0 |
| VII washing | 76.5 |
| VIII washing | 73.5 |
| IX washing | 71.5 |

TABLE 3

Solution A composition (CHCl$_3$/FPVE) treated with CH$_3$(CH$_2$)$_2$OH

| Washing with CH$_3$(CH$_2$)$_2$OH in 1:1 ratio by wt with solution A | FPVE phase components | | |
|---|---|---|---|
| | CHCl$_3$ % w/w | CH$_3$(CH$_2$)$_2$OH % w/w | FPVE % w/w |
| Initial | 2 | — | 98 |
| after I washing | 0.08 | 0.22 | 99.7 |
| after II washing | 0.17 | 0.33 | 99.5 |
| after III washing | 0.25 | 0.25 | 99.5 |
| after IV washing | 0.34 | 0.26 | 99.4 |
| after V washing | 0.42 | 0.28 | 99.3 |
| after VI washing | 0.52 | 0.28 | 99.2 |
| after VII washing | 0.59 | 0.21 | 99.2 |
| after VIII washing | 0.66 | 0.24 | 99.1 |
| after IX washing | 0.69 | 0.31 | 99.0 |

TABLE 4

| Washing with CH$_3$(CH$_2$)$_2$OH in 1:1 ratio by wt with solution A | % weight variation of CHCl$_3$ in FPVE phase (%) |
|---|---|
| I washing | 96.0 |
| II washing | 91.5 |
| III washing | 87.5 |
| IV washing | 83.0 |
| V washing | 79.0 |
| VI washing | 74.0 |
| VII washing | 70.5 |
| VIII washing | 67.0 |
| IX washing | 65.5 |

TABLE 5

Solution A cmposition (CHCl$_3$/FPVE) treated with CH$_3$COOH

| Washing with CH$_3$COOH in 1:1 ratio by wt with solution A | FPVE* phase components | | |
|---|---|---|---|
| | CHCl$_3$ % w/w | CH$_3$COOH % w/w | FPVE % w/w |
| Initial | 2 | — | 98 |
| after I washing | 0.25 | 6.5 | 93.25 |
| after II washing | 0.5 | 6.8 | 92.7 |
| after III washing | 0.38 | 6.7 | 92.82 |
| after IV washing | 0.75 | 6.3 | 92.95 |
| after V washing | 1.13 | 6.7 | 92.17 |
| after VI washing | 1.38 | 7.2 | 91.42 |
| after VII washing | 1.75 | 7.2 | 91.05 |
| after VIII washing | 2 | 7.1 | 90.9 |
| after IX washing | 2.5 | 6.8 | 90.7 |

*: the complement to 100 is H$_2$O.

TABLE 6

| Washing with CH$_3$COOH in 1:1 ratio by wt with solution A | % weight variation of CHCl$_3$ in FPVE phase (%) |
|---|---|
| I washing | 86.6 |
| II washing | 73.2 |
| III washing | 79.6 |
| IV washing | 60.0 |
| V washing | 39.4 |
| VI washing | 25.6 |
| VII washing | 5.7 |
| VIII washing | * |
| IX washing | * |

*: extracting agent saturated with CHCl$_3$ with release of the same in FPVE phase.

TABLE 7

Composition of collected amounts of FPVE solutions treated with extracting agents according to examples 1, 2 and 3

|  | FPVE phase composition | | |
| --- | --- | --- | --- |
| EXTRACTING AGENT TYPE | $CHCl_3$ % w/w | EXTRACTING AGENT % w/w | FPVE % w/w |
| $CH_3OH$ | 0.33 | 0.15 | 99.52 |
| $CH_3(CH_2)_2OH$ | 0.4 | 0.28 | 99.32 |
| $CH_3COOH$* | 1.13 | 6.6 | 92.27 |

*: $H_2O$ traces ≈ 0.1%

TABLE 8

Solution B composition ($CHCl_3$/MCP/FPVE) treated with alcohols

| Washing with alcohols in 1:2 ratio by wt with solution B | FPVE phase components | | | |
| --- | --- | --- | --- | --- |
|  | $CHCl_3$ % w/w | MCP % w/w | alcohol % w/w | FPVE % w/w |
| Initial | 5 | 11.1 | — | 83.9 |
| treatment with methanol | 0.5 | 4.3 | 0.8 | 94.4 |
| treatment with ethanol | 0.7 | 4.1 | 1.2 | 94.0 |
| treatment with sec-buthanol | 0.9 | 2.7 | 4.3 | 92.1 |
| treatment with isopropanol | 0.6 | 2.6 | 1.5 | 95.3 |
| treatment with n-propanol | 0.4 | 1.8 | 0.3 | 97.5 |
| treatment with 2-pentanol | 0.4 | 1.5 | 1.3 | 96.8 |
| treatment with n-decanol | 1.6 | 3.9 | 2.1 | 92.4 |

TABLE 9

| Washing with alcohols in 1:2 ratio by wt with solution B | % weight variation of MCP (%) in FPVE phase | % weight variation of $CHCl_3$ (%) in FPVE phase |
| --- | --- | --- |
| treatment with methanol | 61.3 | 90.0 |
| treatment with ethanol | 63.1 | 86.0 |
| treatment with sec-butanol | 75.7 | 82.0 |
| treatment with isopropanol | 76.6 | 88.0 |
| treatment with n-propanol | 83.8 | 92.0 |
| treatment with 2-pentanol | 86.5 | 92.0 |
| treatment with n-decanol | 64.9 | 68.0 |

TABLE 10

Solution C composition (MCP/FPVE) treated with new $CH_3CH_2OH$

| Washing with $CH_3CH_2OH$ in 1:1 ratio by wt with solution C | FPVE phase components | | |
| --- | --- | --- | --- |
|  | MCP % w/w | $CH_3CH_2OH$ % w/w | FPVE % w/w |
| Initial | 10 | — | 90 |
| after I washing | 3.6 | 0.7 | 95.7 |
| after II washing | 1.0 | 0.5 | 98.5 |
| after III washing | 0.2 | 0.4 | 99.4 |
| after IV washing | ≦0.1 | 0.2 | 99.7 |

TABLE 11

Solution A composition ($CHCl_3$/FPVE) treated with new $CH_3CH_2OH$

| Washing with $CH_3CH_2OH$ in 1:1 ratio by wt with solution A | FPVE phase composition | | |
| --- | --- | --- | --- |
|  | $CHCl_3$ % w/w | $CH_3CH_2OH$ % w/w | FPVE % w/w |
| Initial | 2 | — | 98 |
| after I washing | 0.2 | 0.4 | 99.4 |
| after II washing | 0.0 | 0.4 | 99.6 |
| after III washing | 0.0 | 0.4 | 99.6 |
| after IV washing | 0.0 | 0.4 | 99.6 |

TABLE 12

Solution D composition ($CHCl_3$/MCP/FPVE) treated with alcohols

| Washing with $CH_3CH_2OH$ in 1:1 ratio by wt with solution D | FPVE phase components | | | |
| --- | --- | --- | --- | --- |
|  | $CHCl_3$ % w/w | MCP % w/w | alcohol % w/w | FPVE % w/w |
| Initial | 2 | 10 | — | 88 |
| after I washing | 0.3 | 3.3 | 0.6 | 95.8 |
| after II washing | <0.05 | 1.0 | 0.3 | 98.7 |
| after III washing | 0.0 | 0.4 | 0.2 | 99.4 |
| after IV washing | 0.0 | 0.1 | 0.2 | 99.7 |

TABLE 13

Solution E and F compositions (CFC-113/FPVE) treated with CH₃OH

| Washing with CH₃OH in 1:1 ratio by wt with E and F solutions | FPVE phase components | | |
|---|---|---|---|
| | CFC-113 % w/w | CH₃OH % w/w | FPVE % w/w |
| Initial | 33 | — | 67 |
| after I washing | 14.1 | 0.3 | 85.6 |
| after II washing | 2.7 | 0.1 | 97.2 |
| Initial | 17 | — | 83 |
| after I washing | 7.2 | 0.2 | 92.6 |
| after II washing | 1.9 | 0.1 | 98.0 |

TABLE 14

| EXAMPLE | 10 | 11 (cfr) |
|---|---|---|
| Reaction time (min) | 360 | 275 |
| Rp (g polymer/min) | 5.6 | 7.3 |
| Titre TCAP sol. (g TCAP/ml) | 0.09 | 0.12 |
| Characterization | | |
| MFI (5 kg) (g/10') | 1.0 | 1.6 |
| Tm (II) ° C. | 229 | 230 |
| η (a 1s⁻¹) (Pa.s) | 3.5.10⁴ | 2.2.10⁴ |
| Slope of the shear viscosity/shear rate curve between 1 e 10 sec−1 (Pa.s²) | 2700 | 1400 |
| Mechanical properties 175° C. | | |
| Elastic modulus (MPa) | 15 | 20 |
| Yield stress (MPa) | 1.6 | 1.9 |
| Yield strain (%) | 35 | 48 |
| Stress at break (MPa) | 5.3 | 4.2 |
| Elongation at break (%) | 908 | 900 |

What is claimed is:

1. A process for purifying perfluoropropylvinylether (FPVE), derived from a fluoropolymer synthesis process and containing contaminants, the process consisting of performing one or more liquid—liquid extractions using a $C_1$–$C_{10}$ alcohol or mixture thereof as the extractant, thereby separating the contaminants from the FPVE.

2. The process according to claim 1 wherein a $C_1$–$C_5$ alcohol or mixtures thereof are used.

3. The process according to claim 2 wherein the alcohol is methanol and/or propanol.

4. The process according to claim 1 wherein the ratio value between the alcohols and the perfluoropropylvinylether (FPVE) ranges from 1:20 to 20:1 by weight.

5. The process according to claim 4 wherein the ratio ranges from 1:10 to 10:1 by weight.

6. The process according to claims 1 wherein the perfluoropropylvinylether (FPVE) contains unsaturated hydrogenated, halogenated and perhalogenated substances.

7. The process according to claim 6 wherein the perfluoropropylvinylether (FPVE) originates from the synthesis of ethylene/chlorotrifluoroethylene fluoropolymers.

8. The process according to claim 7 wherein the perfluoropropylvinylether (FPVE) contains methylcyclopentane and/or chloroform.

9. The process according to claim 7 wherein the perfluoropropylvinylether (FPVE) contains one or more polymerization solvents.

10. The process according to claim 9 wherein the polymerization solvent is 1,1,2-trichloro-1,2,2 trifluoroethane.

11. The process according to claim 1, wherein the process is a continuous, semi-continuous or batch process.

* * * * *